(12) United States Patent
Mukdadi et al.

(10) Patent No.: US 9,039,621 B2
(45) Date of Patent: May 26, 2015

(54) NON-INVASIVE ULTRASONIC GINGIVAL TISSUE DIAGNOSIS

(75) Inventors: Osama M. Mukdadi, Morgantown, WV (US); Ahmed M. Mahmoud, Pittsburgh, PA (US); Eros S. Chaves, Morgantown, WV (US); Richard Crout, Morgantown, WV (US)

(73) Assignee: THE UNITED STATES OF AMERICA NATIONAL INSTITUTES OF HEALTH (NIH), U.S. DEPT. OF HEALTH AND HUMAN SERVICES (DHHS), NIH DIVISION OF EXTRAMURAL INVENTIONS AND TECHNOLOGY RESOURCES (DEITR), Washington, DC (US)

( * ) Notice: Subject to any disclaimer, the term of this patent is extended or adjusted under 35 U.S.C. 154(b) by 0 days.

(21) Appl. No.: 13/560,236

(22) Filed: Jul. 27, 2012

(65) Prior Publication Data

US 2013/0029293 A1    Jan. 31, 2013

Related U.S. Application Data

(60) Provisional application No. 61/574,037, filed on Jul. 27, 2011.

(51) Int. Cl.
| | |
|---|---|
| *A61B 8/08* | (2006.01) |
| *A61B 8/12* | (2006.01) |
| *G06T 7/00* | (2006.01) |
| *G06F 19/00* | (2011.01) |

(52) U.S. Cl.
CPC ... *A61B 8/08* (2013.01); *A61B 8/12* (2013.01); *G06T 7/0012* (2013.01); *G06F 19/321* (2013.01); *A61B 8/5207* (2013.01)

(58) Field of Classification Search
USPC .......... 600/437, 438, 443, 459–463; 382/128, 382/171, 173, 276, 282; 433/72
See application file for complete search history.

(56) References Cited

U.S. PATENT DOCUMENTS

| | | | |
|---|---|---|---|
| 2004/0034306 A1* | 2/2004 | Seward | 600/459 |
| 2010/0121191 A1 | 5/2010 | Ariff et al. | |

OTHER PUBLICATIONS

Wagasuki-Sato et al. Advanced Clinical Usefulness of Ultrasonography for Diseases in Oral and Maxillofacial Regions. Int J Dent. Apr. 2010.*

Rudd, et al. "Simulations of Ultrasonographic Periodontal Probe Using the Finite Integration Technique" The Open Acoustics Journal, 2009, 2, 1-19.

Bains, et al. "Application of Ultrasound in Periodontics: Part I" Journal of Indian Society of Peridontology, Year: 2008, Volume: 12, Issue: 2, p. 29-33.

(Continued)

*Primary Examiner* — Parikha Mehta
(74) *Attorney, Agent, or Firm* — Thomas | Horstemeyer, LLP.

(57) ABSTRACT

Disclosed are various embodiments for echoperiodontal imaging. In one embodiment, a system includes a transducer configured to transmit a series of ultrasonic signals at a plurality of corresponding locations along soft tissue of a jaw and receive a plurality of echo signals; and an imaging system controller configured to obtain a plurality of echo signal data of the soft tissue and a plurality of transducer positions, where each echo signal data corresponds to one of the plurality of transducer position.

18 Claims, 19 Drawing Sheets

(56) References Cited

OTHER PUBLICATIONS

Savitha, et al. "Comparative Assesment of Gingival Thickness Using Transgingival Probing and Ultrasonographic Method" Indian Journal of Dental Research, Year: 2005, Volume: 16, Issue: 4, p. 135-139.

Salmon, et al. "Intraoral Ultrasonography: Development of a Specific High-Frequency Probe and Clinical Pilot Study" Clin Oral Invest, DOI 10.1007/s00784-011-0533-z, Published online: Mar. 5, 2011.

Lóst, et al. "Periodontal Ultrasonic Diagnosis: Experiments on Thin Bony Platelets and on a Simulated Periodontal Ligament Space" J. Periodont Res 1988; 23: 347-351.

McCombs, et al. "The Potential of the Ultrasonic Probe" The Journal of Professional Excellence Dimensions of Dental Hygiene, Apr. 2006; 4(4): 16-18.

Lynch, et al. "Ultrasonic Device for Measuring Periodontal Attachment Levels" Review of Scientific Instruments, vol. 73, No. 7, Jul. 2002, 2686-2693.

Cheryl Farr "Ultrasonic Probing: The Wave of the Future in Dentistry" Dentistry Today, Circulation 150,000, vol. 19, No. 3, Mar. 2000.

Hou, et al. "Ultrasonic Periodontal Probing Based on the Dynamic Wavelet Fingerprint" Hou, Rose and Hinders, pp. 1-15.

* cited by examiner

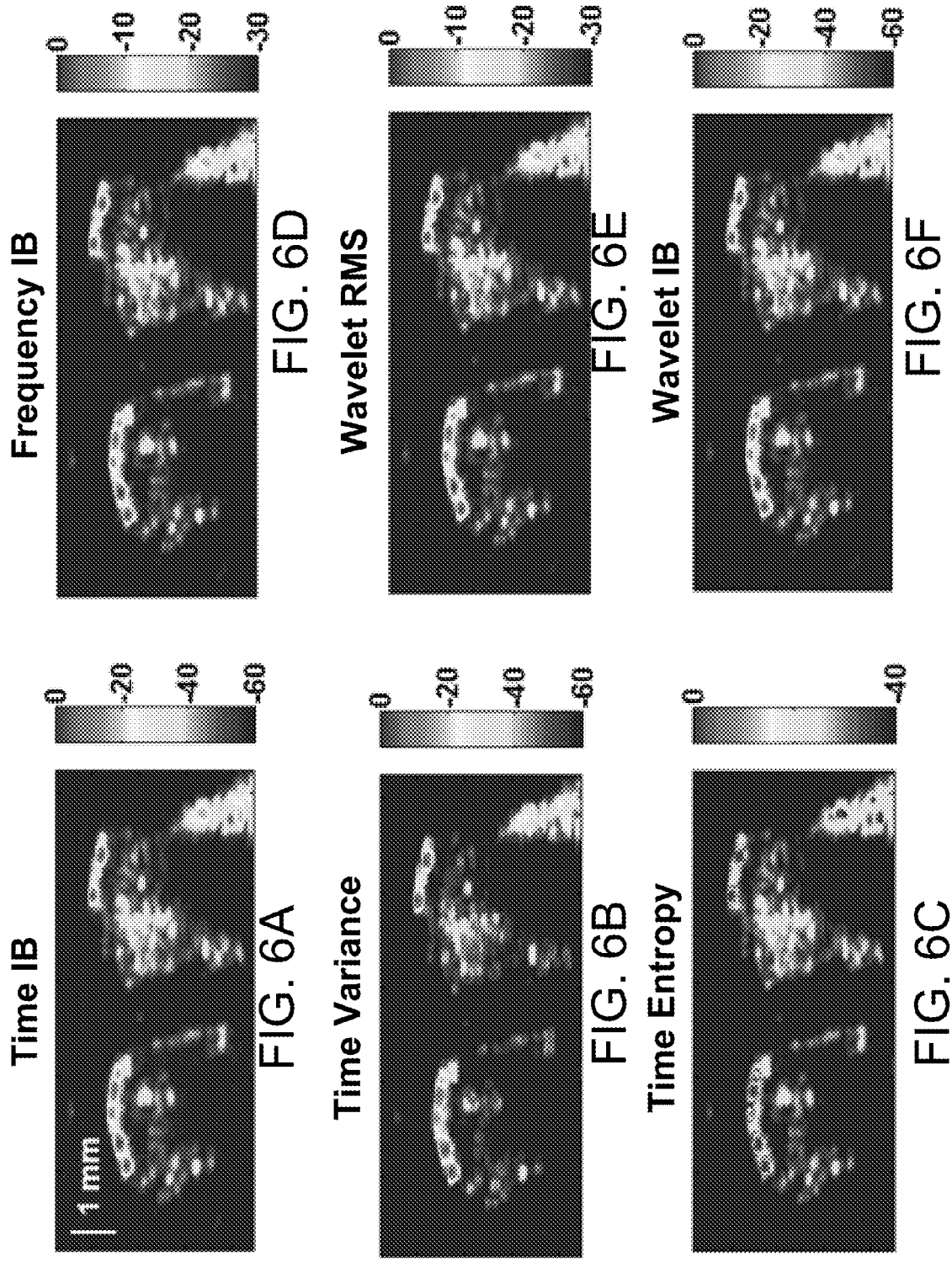

1400 ⇢

POSITION A SAMPLE IN DEGASSED WATER NEAR THE ULTRASOUND TRANSDUCER FOCUS FOR SCANNING WITH THE FREE GINGIVAL SURFACE OF THE SAMPLE FACING THE ULTRASOUND TRANSDUCER
1410

PERFORM SEQUENTIAL ULTRASOUND SCANS PARALLEL TO THE BASE OF THE SAMPLE TO RENDER CROSS-SECTIONAL ULTRASOUND IMAGES IN THE OCCLUSAL PLANE
1420

DETECT HYPERECHOIC AND HYPOECHOIC REGIONS IN THE ULTRASOUND IMAGES TO IDENTIFY PERIODONTAL DEFECTS IN THE GINGIVAL TISSUE
1430

FIG. 13

NON-INVASIVE ULTRASONIC GINGIVAL TISSUE DIAGNOSIS

This application claims priority to U.S. provisional application entitled, "Systems and Methods of Non-Invasive Ultrasonic Gingival Tissue Diagnosis," having U.S. Ser. No. 61/574,037, filed Jul. 27, 2011, which is entirely incorporated herein by reference.

STATEMENT REGARDING FEDERALLY SPONSORED RESEARCH OR DEVELOPMENT

This invention was made with government support under Grant No. R21 DE019561 awarded by the National Institute of Health. The government has certain rights in the invention.

BACKGROUND

Gingivitis is an initial form of periodontal disease. It is the most common gingival inflammation in the oral cavity, and the most prevalent periodontal disease affecting 90% of the population in all age groups. Clinically, gingivitis is characterized by alteration in color, contour, surface texture, and size in the gingival margin around the tooth and in more advanced stages, presence of bleeding on touch or spontaneously.

Examination and diagnosis of gingivitis is usually a clinical subjective assessment performed by dentist. It is based upon clinical alterations in color, size, form, position, consistency, texture, and contour. Clinical diagnosis of gingivitis is based upon a descriptive clinical assessment of extent and severity. The use of periodontal probing contributes to a dichotomous assessment of presence or absence of bleeding upon probing. Bleeding on probing after stimulation has been the strongest evidence of gingival inflammation in clinical, histopathologic, and bacteriologic studies. However, the evidence of bleeding on probing is still dependent on clinical interpretation related to definition of clinical probing and pocket depth.

The importance of properly diagnosing and treating gingivitis is critical for early individual preventive treatment. Without treatment, the persistency of this inflammatory process progresses to irreversible destruction of the periodontal attachment around the tooth leading to more advanced periodontitis and tooth loss.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 6A-6F are diagrams of ultrasound parametric images for the same cross-section of the tissue samples from FIG. 4 in accordance with various embodiments of the present disclosure.

FIGS. 11-16 are flow chart diagrams illustrating various operations and methods of the imaging system of FIG. 1 in accordance with various embodiments of the disclosure

DETAILED DESCRIPTION

Embodiments of the present disclosure facilitate diagnosis of gingival soft tissue using ultrasound technology in which inflammatory conditions such as increased cellular infiltration and a decrease in collagen tissues and fibers, as well as thickening of epithelial cells may be identified by ultrasound imaging. In accordance with the present disclosure, high-resolution ultrasound imaging can assess and quantify differences in soft tissues from healthy to diseased stages.

Therefore, embodiments of the present disclosure use high-resolution 2D and 3D ultrasound imaging in quantifying the gingival inflammation and other diseases in the soft tissues around teeth. Exemplary methods of the present disclosure, in some embodiments, are based on advanced signal processing of ultrasound RF data in time-, frequency-, and wavelet-domains. Such quantitative ultrasound imaging techniques provide a non-invasive tool for assessing gingival inflammation in vivo or in vitro.

Figure 1:
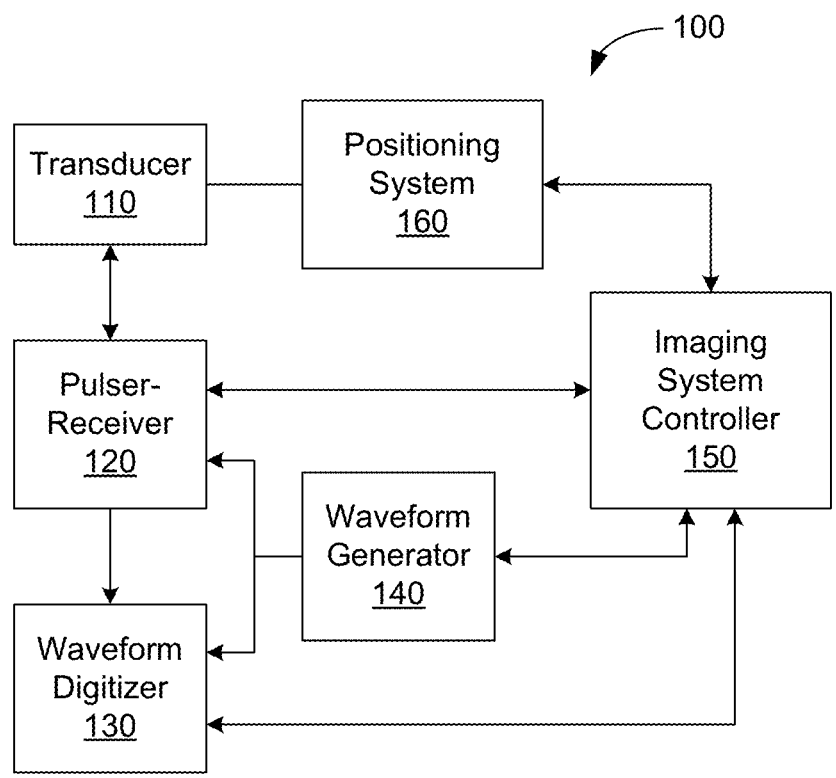
FIGS. 1 and 2 are graphical representations of an exemplary imaging system 100 in accordance with various embodiments of the disclosure.

Referring to FIG. 1, shown is a graphical representation of an exemplary imaging system 100 according to various embodiments of the disclosure. The imaging system 100 of FIG. 1 includes an ultrasonic transducer 110, which is used for both transmission of ultrasound signals and reception of the reflected (or echo) signals. In some embodiments, separate transducers may be used for ultrasound transmission and reception. Alternatively, one-dimensional or two-dimensional arrays of transducers 210 (FIG. 2) may be utilized.

The transducer 110 is in communication with a pulser-receiver unit 120. For example, the transducer 110 is connected to a transmit/receive port of the ultrasound pulser-receiver 120. The pulser-receiver 120 may be operated in a pulse-echo mode to provide impulses for use as the excitation signal for the transducer 110. In one embodiment, negative impulses are provided for the excitation signal. The pulser-receiver 120 may include pre-amplification and/or amplification of the excitation signal. For example, the excitation signal may be generated and amplified using a general purpose ultrasonic pulser-receiver such as, but not limited to, an Olympus Model 5900PR pulser-receiver. An exemplary no-load transmission output of the pulser-receiver 120 has an amplitude of 175 Volts with a rise time of two nanoseconds. The pulser-receiver 120 may provide the excitation signal to stimulate the ultrasound transducers 210 over a wide range of frequencies. For example, frequencies in the range of about 10 MHz to about 120 MHz may be utilized.

The excitation signal is synchronized with the data acquisition using a common trigger signal generated by a waveform generator 140. Received RF signals are preamplifier and filtered, then fed to a high-speed waveform digitizer 130 (e.g., operating at 1 GHz). The waveform digitizer 130 is synchronized with the transducer excitation signal to coordinate digital acquisition of the echo signal. In some embodiments, the excitation signal from the pulser-receiver 120 is synchronized with a data acquisition trigger input of the waveform digitizer 130 using a signal generated by the waveform generator 140. An exemplary waveform generator 140 may be, but is not limited to, a computer controlled function generator In the embodiment of FIG. 1, an imaging system controller 150 provides system control and synchronization of the pulser-receiver 120, waveform digitizer 130, and/or waveform generator 140 during transmission of the ultrasonic signals and acquisition of the echo signals. In embodiments where a transducer array 210 is utilized, the imaging system controller 150 may also be in communication with the array interface 220 for system control and synchronization. The imaging system controller 150 may be a computer-based system, processor-containing system, or other hardware system that is configured to control and synchronize the imaging system 100 and/or control image processing.

The imaging system controller 150 of certain embodiments of the present disclosure can be implemented in hardware, software, firmware, or a combination thereof. In the preferred embodiment(s), the imaging system controller 150 is implemented in software or firmware, i.e., instructions that are stored in a memory and that is executed by a suitable instruction execution system. If implemented in hardware, as in an alternative embodiment, the imaging system controller 150 can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

In some embodiments, the imaging system 100 also includes a positioning system 160 for movement and positioning of the transducer 110. For example, the positioning system 160 may be a two-axis (providing two degrees of translation) positioning system and/or three-axis (providing three degrees of translation) positioning system. Also, in an alternative embodiment, free hand scanning can be performed with the transducer 110 attached to a position tracker (6 degrees of freedom) for 3D reconstruction.

In one embodiment, the positioning system 160 is a high-precision positioning system (such as, but not limited to, those produced by Danaher Corp.) with a positioning resolution down to one micrometer. The positioning system 160 includes a positioning controller for a controlling servo amplifier or stepper motor to adjust the positioning of the transducer 110 along each axis. Alternatively, a robotic arm may be used in the positioning system 160. Alternatively, transducer(s) may be positioned manually or freehand. In other embodiments, positioning system 160 provides translation along a single axis.

The imaging system controller 150 synchronizes the positioning system 160 with the data acquisition by the waveform digitizer 130 to collect the ultrasound signals. In some embodiments, the ultrasound signals are collected continuously "on the fly" during the transducer 110 movement (e.g., down to 10 micrometers apart). Alternatively, the ultrasound signals may be collected in a step-wise fashion. Transducer 110 position information corresponding to the echo signal data acquisition location may also be collected. In one embodiment, the transducer position is acquired a predetermined time before collecting the echo signal. In other embodiments, the position of the transducer 110 is obtained a predetermined time after transmission of the ultrasonic signal. Alternatively, the transducer position may be the average of the transmission position and acquisition position. In some embodiments, the position is approximated based upon the speed and direction of the transducer motion.

Both RF signals and spatial locations are collected from the field of view (FOV) during the transducer 110 movement. During the 3D acquisition, the positioning system 160 moves the transducer 110 further steps in the elevation direction and the lateral scanning process is repeated. Alternatively, the transducer 110 may be moved manually or freehand. An elevation step size down to 100 μm could be used; however, the system 100 can reach smaller step size down to 10 μm based on the FOV. The system 100 can also be programmed with various scanning profiles, and for each profile the operator shall determine the FOV parameters in the axial, lateral, and in the elevation. Also, the operator is able to determine the lateral acquisition speed (frame-rate) that affects distance between RF signals and the elevation step size. Currently, the whole scanning process could be completed in less than 30 seconds using a low frame-rate of 1 frame per second (FPS) for an area of 15 mm (lateral)×5 mm (elevation). In this application, this frame rate is considered adequate for such a stationary object, and is preferred for patient comfort rather than using high-speed. After completing the acquisition process, the data is transferred for post processing and image reconstruction.

In one embodiment, in order to obtain a high-resolution B-mode ultrasound images, several signal and image processing algorithms are applied to the high-frequency echo signals. The imaging system 100 provides access to ultrasound data at all processing stages including synthetic aperture focusing (SAF), envelope detection, and the final B-mode processed images. The exemplary values of the axial and lateral resolutions are approximately measured to be 24 μm and 123 μm, respectively, using a 55 MHz ultrasound transducer 110, in one embodiment.

Note that the system design can be altered in other embodiments to include using an array 210 of ultrasound transducers of different shapes and geometries, scanning from inside or outside a subject's mouth with proper ultrasound coupling, adopting freehand scanning with various position tracking.

Figure 2:
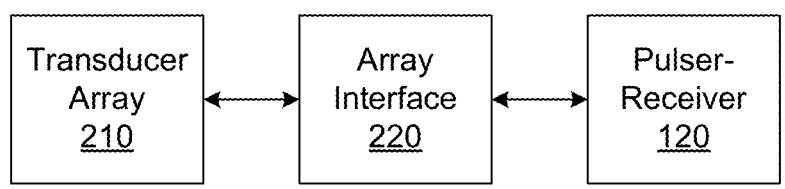

Referring now to FIG. 2, one-dimensional or two-dimensional transducer arrays 210 may be used for transmission of the ultrasound signals and reception of the echo signals. A transducer array 210 may be a linear, curvilinear, or phased array. An array interface 220 may be included between the transducer array 210 and the pulser-receiver 120. The array interface 220 is configured to coordinate application of excitation signals to the transducers of the array 210 and submission of the echo signal received by the transducers of the array 210 to the pulser-receiver 120. The array interface 220 may include a switching matrix that controls the transmit/receive operation and the number of active transducer elements that are working in unison (the group thereby determining the aperture size) and an analog beamforming circuit that controls transmit and receive delays. In one embodiment, the array interface 220 is included in the pulser-receiver 120. In an alternate embodiment, each of a plurality of pulser-receivers 120 may supply a corresponding transducer in the array 120. The plurality of pulser-receivers 120 would then be controlled to coordinate transmission and reception by each transducer.

Figure 3:
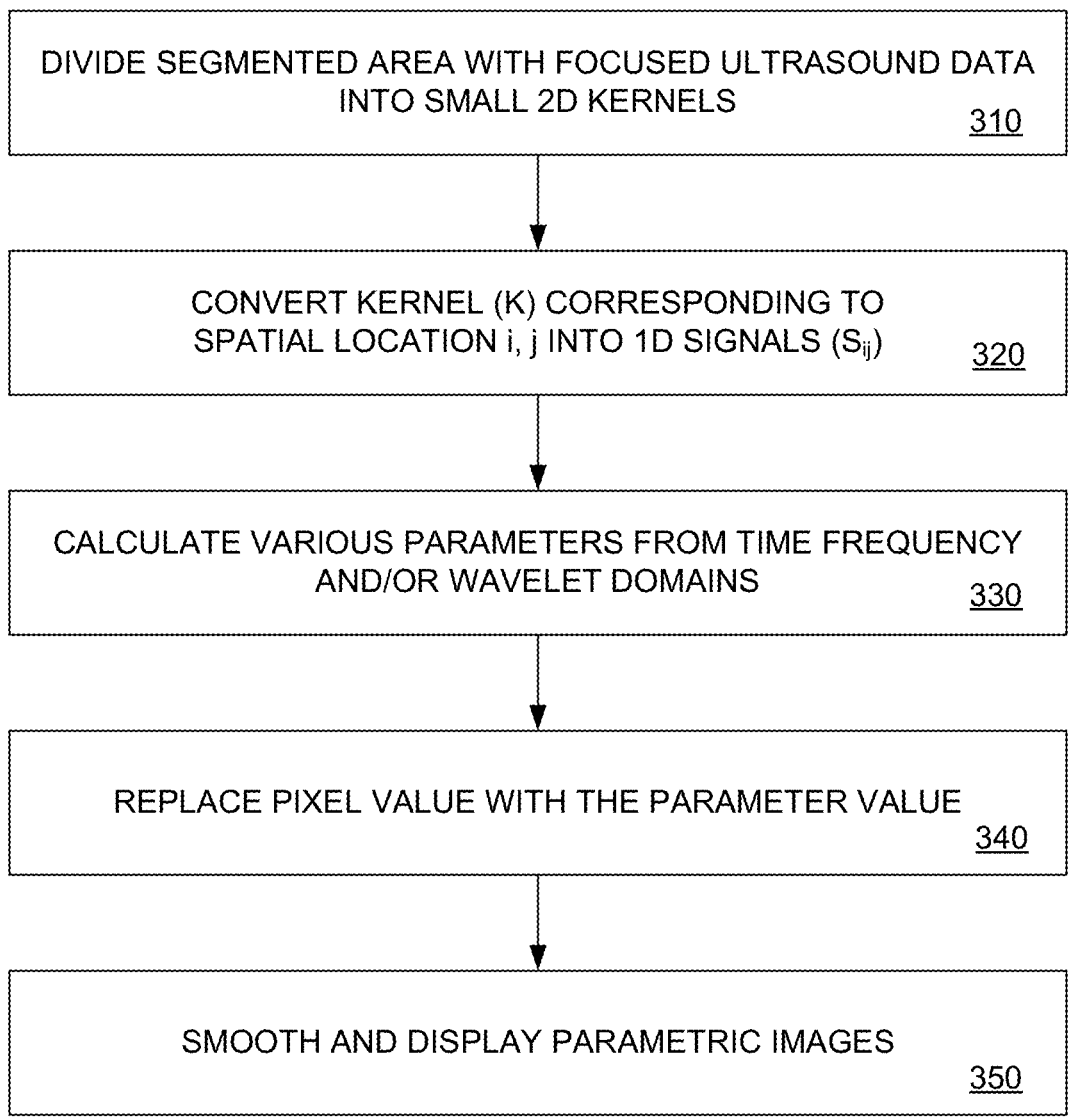
FIG. 3 is a diagram of a flow chart describing an embodiment of an exemplary procedure of a tissue classification technique in accordance with various embodiments of the disclosure.

FIG. 3 is a diagram of a flow chart describing an embodiment of an exemplary procedure of a tissue classification technique, in one embodiment. First, a region of interest (ROI) is segmented and extracted from the raw ultrasound data after focusing. Then, the ROI is divided into 2D kernels of small size, such as 0.15 mm×0.15 mm with approximately 90% overlapping, in block 310. To reconstruct parametric images, a vector $S_{i,j}$ is generated for each spatial location (i,j) within the ultrasound image, in block 320. This vector is reconstructed from the neighborhood pixels $P_{i,j}$ within the kernel $K_{i,j}$, and defined as:

$$S_{i,j} = \left[ P_{i-\frac{n}{2}, j-\frac{m}{2}} \ldots P_{i,j} \ldots P_{i+\frac{n}{2}, j+\frac{m}{2}} \right], \quad (1)$$

where n+1 and m+1 are the kernel length and width in pixels, respectively. Several $S_{i,j}$ vectors are reconstructed from raw ultrasound data after focusing for each spatial location within the ROI. Each vector is considered as a 1D signal that contains embedded information about the neighborhood characteristics used to extract different parameters in time-, frequency-, and wavelet-domains, in block 330. In the following, S is used as a general notation for signals correspond to any spatial location.

In time-domain, ultrasound data is first normalized using reference echo, and then several parameters are calculated. These time parameters include the time-domain integrated backscattering ($T_{IB}$), time variance ($T_{var}$), and time entropy ($T_E$). The time-domain integrated backscatter ($T_{IB}$) parameter is evaluated as the average power of ultrasound backscattered signals and is described in decibel (dB) as:

$$T_{IB} = 20 \log_{10} \left( \frac{\int_0^T S^2 \, dt}{\int_0^T S_0^2 \, dt} \right), \quad (2)$$

where S is the signal voltage within the kernel, $S_0$ is the smallest voltage the system could detect, and T is the integral interval. The second parameter is the time variance ($T_{var}$), which measures the dispersion of signal samples around their mean value evaluated as:

$$T_{var} = \frac{1}{(n+1)(m+1)-1} \sum_{x=1}^{(n+1)(m+1)} (S_x - M)^2 \quad (3)$$

where x is the sample number and M is the mean value of S. In addition to these parameters, Shannon entropy of S is adopted as a parameter sensitive to the RF energy distribution within a ROI in ultrasound imaging. Non-normalized Shannon entropy ($T_E$) of S is used and calculated as:

$$T_E(S) = -\Sigma_x S_x^2 \log(S_x^2), \quad (4)$$

where S is the envelop signal and $S_x$ are the coefficients of S in an orthonormal basis. Note that $T_{var}$ and $T_E$ are evaluated using the envelop signals after normalization.

The next parameter is extracted from the frequency response of the RF signals, such as ultrasound integrated backscatter ($F_{IB}$). Additionally, other parameters such as the variance ($P_{var}$) and the maximum amplitude ($P_{max}$) of the power spectral density (PSD) of signal S can be used for characterization in addition to $F_{IB}$ in accordance with the present disclosure. Here, similar procedures are followed where Burg algorithm is used to estimate the PSD of signal S for each spatial location ($PSD_{i,j}$). The PSD is estimated using Burg autoregressive (AR) prediction model for the signal S. In accordance with the present disclosure, the AR spectrum is calculated using a fast Fourier transform (FFT) of 1024 length, determined based on the signal length, and a $12^{th}$ order AR model after applying hamming window on the time signal. In one embodiment, $F_{IB}$ is evaluated as the normalized average power calculated as the integral of PSD over the transducer frequency bandwidth with respect to the PSD of a perfect reflector ($PSD_{Ref}$), which is described as:

$$F_{IB} = 10 \log_{10} \left( \frac{\int PSD \, df}{\int PSD_{Ref} \, df} \right). \quad (5)$$

In various embodiments, after estimating the PSD in dB, it is subtracted from $PSD_{Ref}$ in dB. Then, a set of frequency parameters are extracted including the maximum power ($P_{max}$), variance ($P_{var}$), etc. The last set of parameters is calculated from the approximation coefficients of wavelet Daubechies 3 (db3). This kind of wavelet decomposition is widely used and has been previously utilized in ultrasound image decomposition. Wavelet parameters such as the root mean square value (RMS) of the approximation signal ($W_{rms}$) and the integrated backscatter ($W_{IB}$) may be used in accordance with the present disclosure. Generally, RMS is a statistical measure of the magnitude of varying quantity. The RMS of the approximation signal ($W_{rms}$) is evaluated as:

$$W_{rms} = \sqrt{\frac{\sum_{n=1}^{N} W_n^2}{N}}, \quad (6)$$

where $W_n$ is the wavelet approximation coefficient number n in W reconstructed from the ROI, and N is the total number of coefficients in W. The parameter $W_{IB}$ is evaluated using wavelet decomposition and is defined as:

$$W_{IB} = 20 \log_{10} \left( \frac{\int_0^K W^2 \, dk}{\int_0^K W_{Ref}^2 \, dk} \right), \quad (7)$$

where $W_{Ref}$ is the wavelet coefficients of the reference echo. Since the first wavelet approximation has been used in this disclosure, K (the integral interval length) equals T/2. In other embodiments, further levels of wavelet decomposition, i.e 2nd down to 8th, may be adopted. Also, other types of wavelet functions may be used.

Parametric ultrasound images are constructed by calculating and assigning the value of each parameter in any domain to the center pixel(s) of the kernel, in block 340. These procedures are repeated for all kernels within the ROI selected for parametric analysis using an overlapping of approximately 90% to form parametric images for the parameters. In block 350, the parametric images are smoothed and displayed by the imaging system 100. Note, in various embodiments, these quantitative ultrasound techniques could adopt parameters other than the abovementioned ones in all domains; one or more parameter could be fused or combined to improve the diagnosis process, and the overlapping ratio range could range 0-99%.

For embodiments of the imaging system 100, representative parameters from each domain are used to reconstruct high-resolution parametric images including: time integrated backscatter ($T_{IB}$), time variance ($T_{var}$), time entropy ($T_E$), frequency integrated backscatter ($F_{IB}$), wavelet RMS ($W_{rms}$), and wavelet integrated backscatter ($W_{IB}$) with dynamic ranges up to 60 dB. These ranges are selected based on the parameters' values for optimum visualization.

Figure 4:
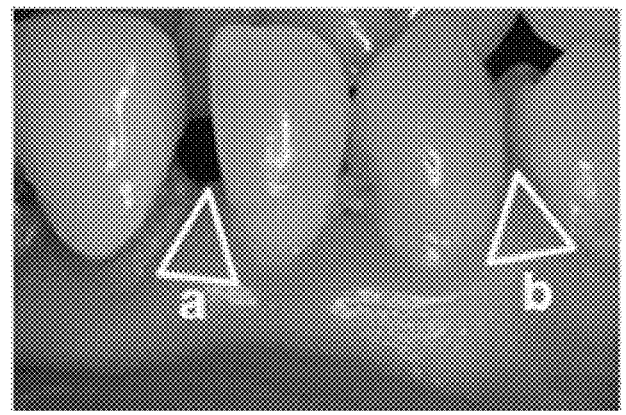
FIG. 4 is an optical image highlighting approximately the regions where the gingival tissue samples were extracted in subsequent in vitro imaging analysis in accordance with various embodiments of the present disclosure.

For in vitro testing purposes, two gingival tissue samples (samples "a" and "b") were extracted from a subject diagnosed with chronic generalized severe periodontitits and different degrees of gingival inflammation. The optical image in FIG. 4 shows the approximate regions from where samples "a" and "b" were extracted as from the free gingival surface and down towards the connective tissue beneath the two triangles superimposed.

Sample "a" is gingival tissues between tooth #'s 7 and 8 with severe gingival inflammation characterized by redness, edematous appearance, loss of papilla, bleeding on clinical probing, and probing depth >5 mm with clinical attachment loss ranging from 7 to 8 mm. While, sample "b" is from interproximal gingiva between tooth #'s 5 and 6 presenting pink color with minor change in the margin closer to the tooth surface, pointed papilla, some stippling, reduced edema, and probing depth ranging from 2-4 mm with clinical attachment loss ranging from 1-2 mm.

Figure 5:
FIG. 5 is a diagram of an ultrasound B-mode image for cross-sections of the tissue samples from FIG. 4 in accordance with various embodiments of the present disclosure.
Figure 7A:
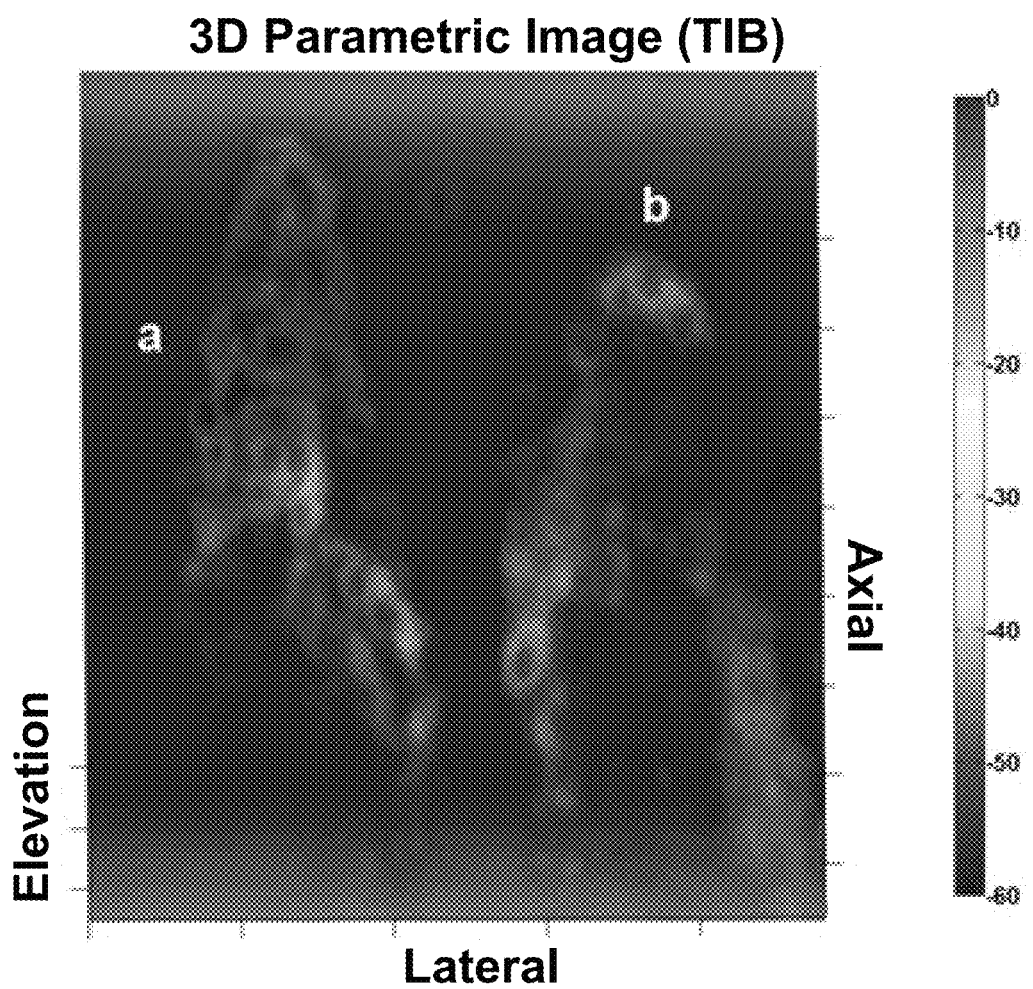
FIGS. 7A-7D are diagrams of ultrasound 3D parametric images for the tissue samples from FIG. 4 in accordance with various embodiments of the present disclosure.
Figure 7B:
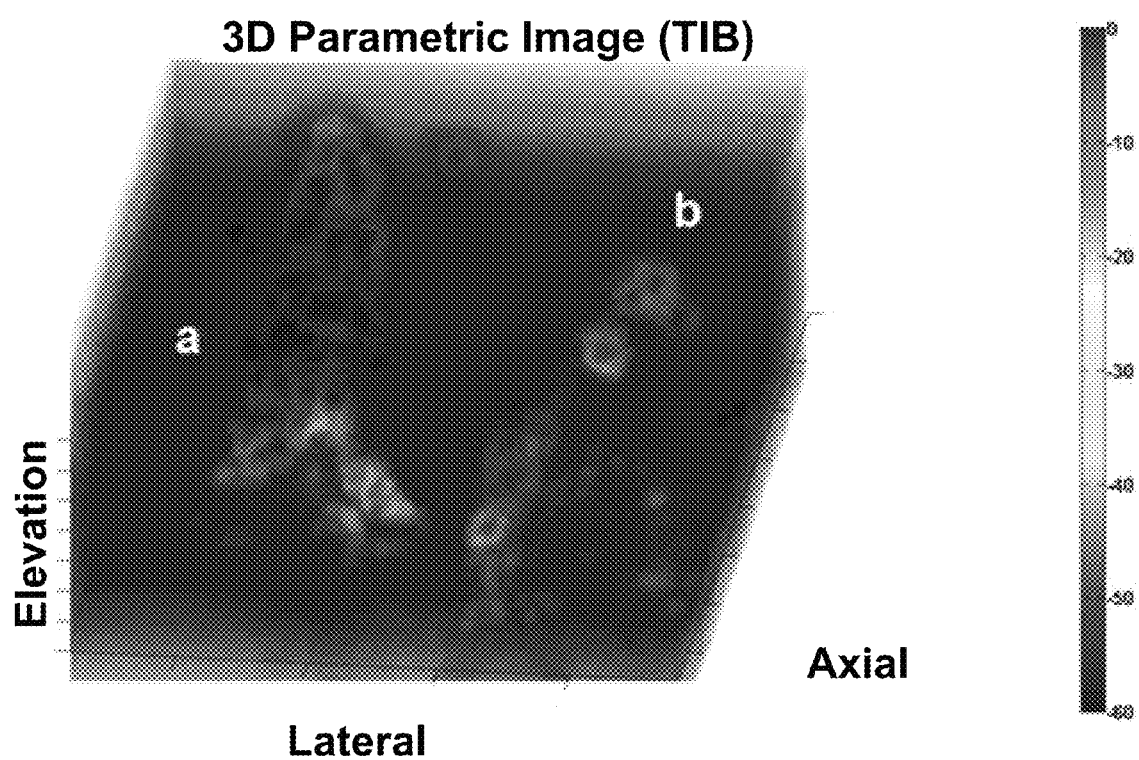
Figure 7C:
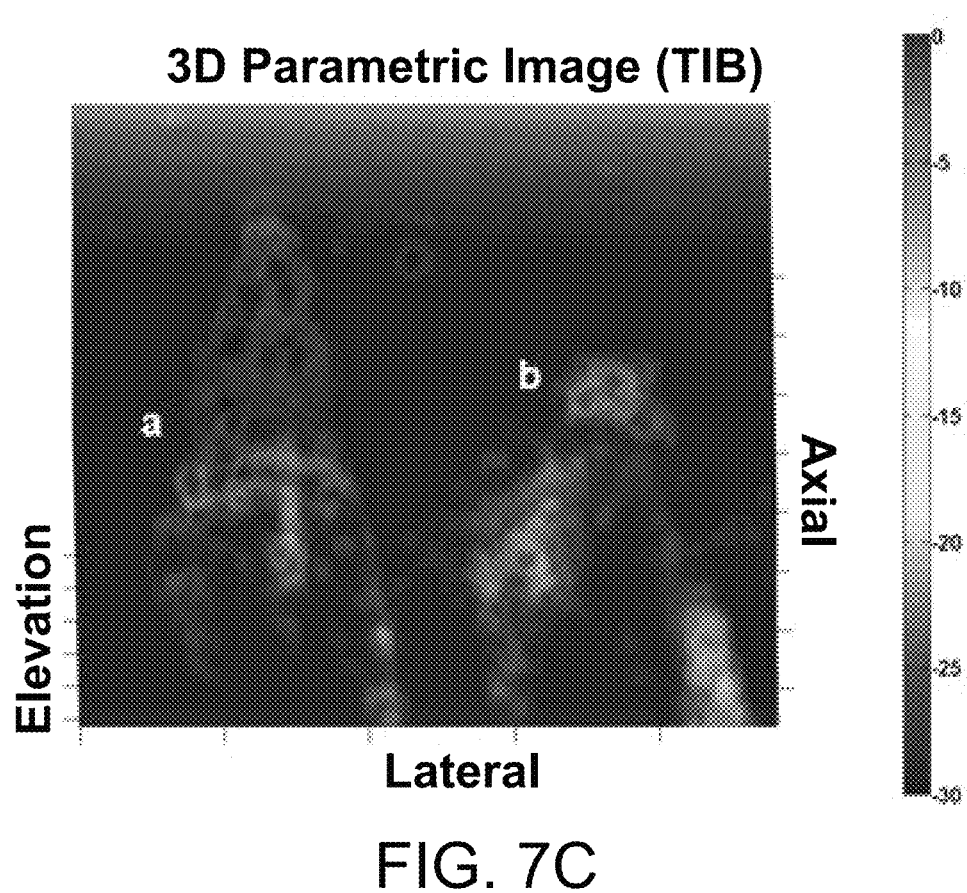
Figure 7D:
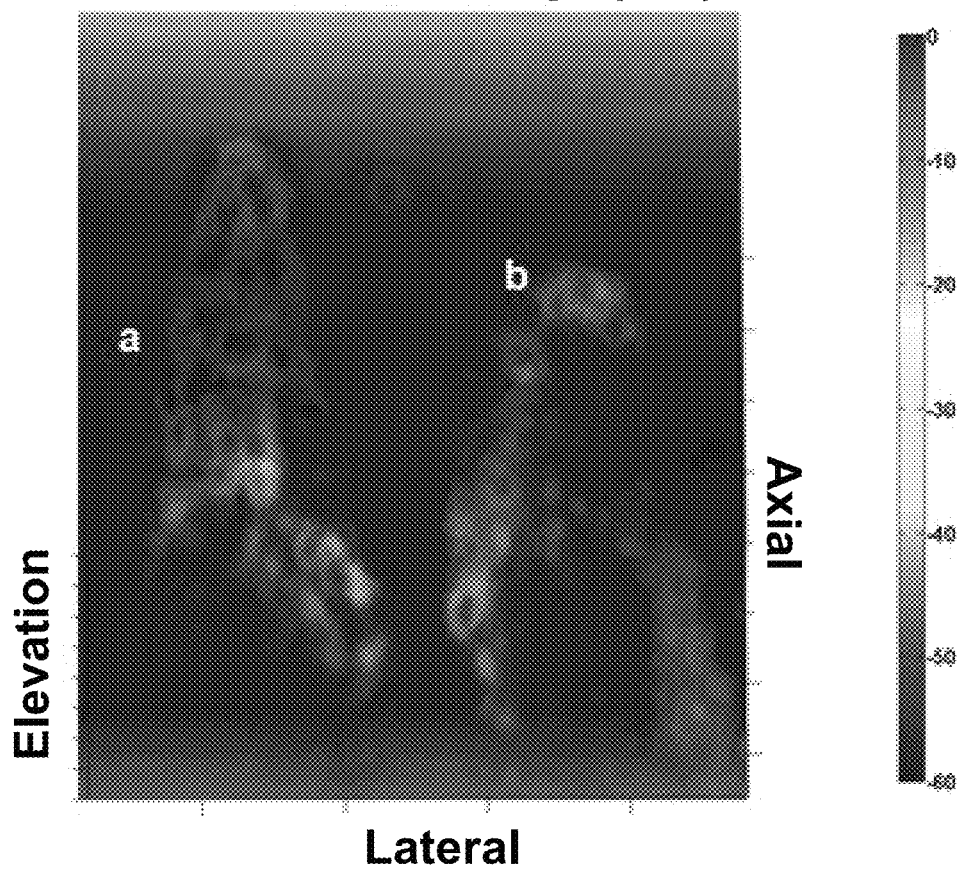

Samples "a" and "b" were placed in degassed water near the ultrasound transducer focus for scanning with the free gingival surface facing the ultrasound transducer 110. Sequential 2D ultrasound scans were performed parallel to the base of the two samples to render cross-sectional ultrasound images in the occlusal plane. In an exemplary test, more than 150 ultrasound scans were acquired 100 µm apart with an average distance between adjacent RF signals of 13.5 µm. A sampling rate of 400 MHz was used during this exemplary test to acquire received RF signals from a transducer 110 of frequency range (25 MHz-75 MHz). Accordingly, FIG. 5 shows an ultrasound B-mode image for two cross-sections near the base for samples "a" and "b", as labeled. The B-mode reconstruction procedures were similar to those described in U.S. Patent Application Publication 2010/0210943 which is incorporated by reference in its entirety. Note that the optical image (FIG. 4) is for the upper jaw and is inverted to match the sections shown in (FIG. 5). Please further note that the quality of these images and/or other depicted images may not be capable of being accurately reproduced within the pages of the present document. For example, actual images provide color representations that are not capable of being represented in the black and white images/drawings of the present document.

In acquired B-mode images, sample "a" generally shows less homogenous echo patterns than sample "b" in the outer regions. Based on a histological study of the gingival tissue samples, these echo patterns in the outer regions of both samples correspond to the oral epithelial layer with the hyper-echoic response compared to the connective tissue layer beneath. Also, it is observed that sample "a" shows larger hyper-echoic lesion (white spots) on the top part than the corresponding lesion in sample "b". Additionally, sample "a" shows an anechoic lesion where the arrow indicates in FIG. 5 in the middle of tissue patterns. Based on a histological study, this anechoic response may correspond to a cyst.

As shown in the images, it is notable that the in the areas having hypo-echoic effect and appearing as dark regions in the images, correspond to inflammation vicinity. Moreover, hyper-echoic regions that are displayed as bright regions in the image correspond to the dense epithelium exhibiting infiltrating inflammatory cells into the inner connective tissue.

Since gingivitis is characterized by infiltration of particularly acute inflammatory cells into the epithelium, the outside lining of the gingival connective tissue that surrounds the teeth, this inflammation progression cause changes in the local acoustic impedances, which produces reflections. The hyper-echoic behavior in the ultrasound images demarcates healthy dense epithelium from inflamed gingiva. Moreover, hypo-echoic regions in B-mode ultrasound images indicate high attenuation of inflamed gingiva. If treatment is not provided, the progression can lead to further loss of integrity of the epithelium eventually affecting the underlying connective tissue and bone. As more inflammatory cells are noted with increased disease, the ultrasound can quantify these changes.

As discussed previously, representative parameters from a plurality of domain are used to construct high-resolution parametric images. FIGS. 6A-6F show parametric images reconstructed using $T_{IB}$, $T_{var}$, $T_E$, $F_{IB}$, $W_{rms}$, and $W_{IB}$ parameters, respectively. It is observed that the use of parametric images improves the contrast resolution and can be used to characterize different tissue components. In these images, sample "a" exhibits higher parameters' values that are distributed on larger area than sample "b", in particular within the free gingival area (near the transducer 110). Additionally, the abovementioned cyst in sample "a" appears in all images as a region of lower parameters' values than the surrounding epithelium. Generally, it is noticed that the average parameters' values per area in the case of severe inflammation (sample "a") are higher than those in mild inflammation case (sample "b").

Similar findings can be reached when using the 3D parametric images shown in FIGS. 7A-D reconstructed using sample parameters including $T_{IB}$, $T_{var}$, $F_{IB}$, and $W_{IB}$, respectively. In the four different views of the 3D parametric images, it is observed that there is a possible correlation between the gingival diagnosis from one side and the distribution and dB values of all parameters, from the other side.

In a preliminary in vivo test, ultrasound scanning is performed to image the mandible of a healthy male subject (37 years old). The subject has no periodontal defect deeper than 3 mm without bleeding on probing and oral soft tissues within normal limits. Prophylaxis is performed at baseline (week 0) and immediately before ultrasonic evaluation and clinical pictures. The subject was instructed to abstain of mechanical plaque control in his upper and lower anterior teeth (#6, 7, 8 and 26, 27 and 28) by using a stent that would cover these teeth during tooth brushing. No effort was made to eliminate swishing water after brushing and the subject had the habit of chewing gum during the day.

In the exemplary test, a 14-MHz linear array transducer 210 (e.g., an extraoral transducer probe) was placed outside the mouth on the facial tissue, where ultrasound gel was used for the coupling. Inside the mouth, the subject was instructed to place a thin layer of commercially available sugar-free gelatin snack as the coupling from the other side, from the facial tissue to gingival tissue.

Figure 8A:
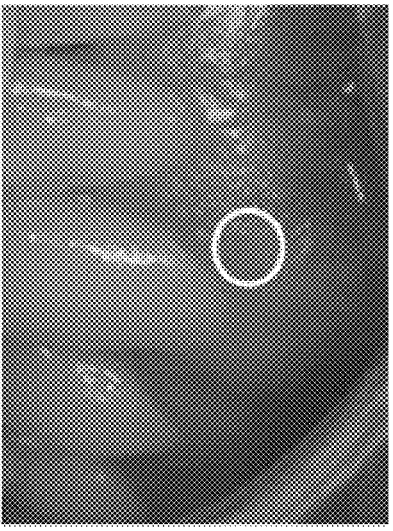
FIGS. 8A-8B are table diagrams depicting changes that occurred in the gingival tissue thickness of a subject over a 4-week period using clinical optical pictures and ultrasound images acquired in vivo using an extraoral probe in accordance with various embodiments of the present disclosure.
Figure 8B:
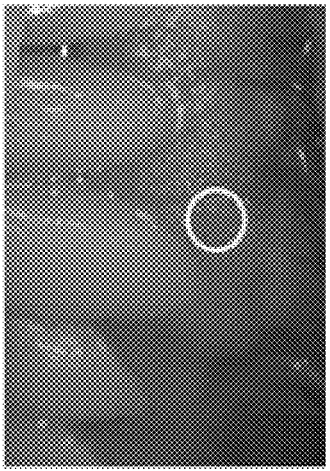

The table of FIGS. 8A-8B describes the changes that occurred in the gingival tissue thickness of the subject over 4-week period starting at week 0 (w0). The first column in the table of FIGS. 8A-8B shows the approximately measured gingival tissue thickness using the ultrasound images in column three. The ultrasound images show cross-sectional views including the gingival tissue between the arrows superimposed near the marginal gingiva. The region between these arrows is approximately a cross-section view in the gingival tissue beneath the circle superimposed on the optical images in the second column of FIGS. 8A-8B.

From the acquired images, it is observed that the gingival thickness is 1.88 mm at w0 (in FIG. 8A), right after the prophylaxis, and then decreases to 1.78 mm at w1 (in FIG. 8A) when the tissue was recovered as of the response of the prophylaxis process. At w2 (FIG. 8B), the gingival thickness started to increase due to the isolation of such area from tooth brushing. This effect continues till w4 (FIG. 8B) when the gingival thickness increases to 2.24 mm. These changes are noted to be difficult to track by the optical images in column two.

Figure 9A:
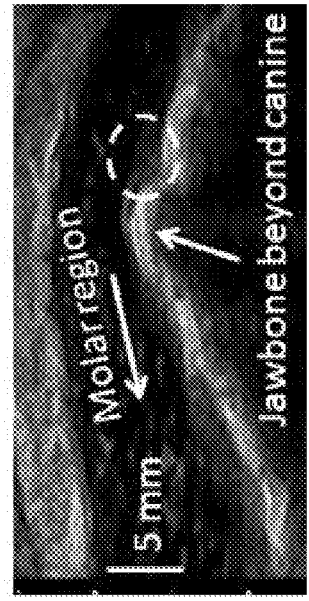
FIGS. 9A-9B are table diagrams depicting changes that occurred in the gingival tissue echogenicity of a subject over a 4-week period using clinical optical pictures and ultrasound images acquired in vivo using an extraoral probe in accordance with various embodiments of the present disclosure.
Figure 9B:
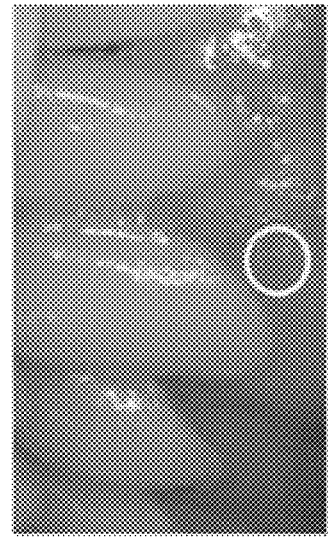

Not only are gingival thickness changes observed in the ultrasound images acquired from the ROI described in FIGS. 8A-8B, but also changes in the tissue echogenicity are observed in ultrasound images (FIGS. 9A-9B).

At w0 (FIG. 9A), the parametric image reveals a cross sectional view of the soft tissue including the gingival tissue between the two opposing arrows superimposed near the marginal gingiva, while the single arrow represents the jaw bone at the canine tooth. It is noted that that the interface between the bone and soft tissue appears as a very bright boundary (in the original acquired images), because this interface has a high reflectivity for ultrasound waves. Also, very little appears below the bone line, as the ultrasound waves cannot penetrate and reflect back from the bone because of its high attenuation nature with respect to the soft tissue. From the image, the gingival thickness is measured to be 5 mm.

The B-mode images in FIG. 9B at w3 and w4, for different gingival cross-sections within the ROI highlighted by the circle on optical images, show higher reflections within the gingival tissue surface than those in w0-2 (FIG. 9A and FIG. 9B). This may be an indication of changes in the gingival tissue properties due to the early expected inflammation and matches findings from in vitro testing. Without treatment, the persistence of this inflammatory process may progress to irreversible destruction of the periodontal attachment around the tooth leading to the more advanced stage (periodontitis), resulting in the possible loss of the tooth.

X-rays are unable to resolve such subtle soft-tissue interfaces and determine if the disease has spread to the underlying bone. Ultrasound technology has the potential to provide great help in further evaluation of the subtle differences. Ultrasound has the advantage over manual probing in being completely painless, and it also has the ability of providing much better resolution than the ±1 mm ascribed to the current diagnostic gold standard. Ultrasound imaging is a very safe modality compared to those involving ionizing radiation, such as X-ray and nuclear medicine.

In addition to extraoral techniques, intraoral imaging techniques may also be considered. For intraoral imaging techniques, the transducer 110 comprises an intraoral linear probe, where the probe is situated inside the patient's mouth, specifically over the gum. One embodiment of the intraoral probe comprises a linear array side fire ultrasound probe having an imaging head with a length of 3 cm, width of 1 cm, and a height of 1.8 cm. The dimensions are similar to a regular tooth brush. The overall length of the probe is 19 cm, in an exemplary embodiment.

Also, in one embodiment, the probe has 80 piezoelectric elements separated by 300 µm pitch. Center frequency is 8 MHz with 70% bandwidth. Probe's acoustic lens is made from a biocompatible mixed silicone material. A linear array 210 is used to attain the optimal beam uniformity and image quality.

During a set of testing trials, the intraoral probe was connected and configured to the same ultrasound unit used in the previously described extraoral imaging technique. Here, the intraoral probe can be positioned almost like a regular tooth brush. A major difference is that the probe head is to be located in front of the gum not the teeth, to image the gingival soft tissue. To remove air bubbles and match the acoustic impedance between the probe and the gingival tissue, the oral cavity in front of the area to be imaged was filled with gelatin dessert and then the probe was inserted into it. Other coupling methods were also available to be used, such as water, or deformable solid gels, for cases that could not use gelatin based desserts for a clinical reason.

Figure 10:
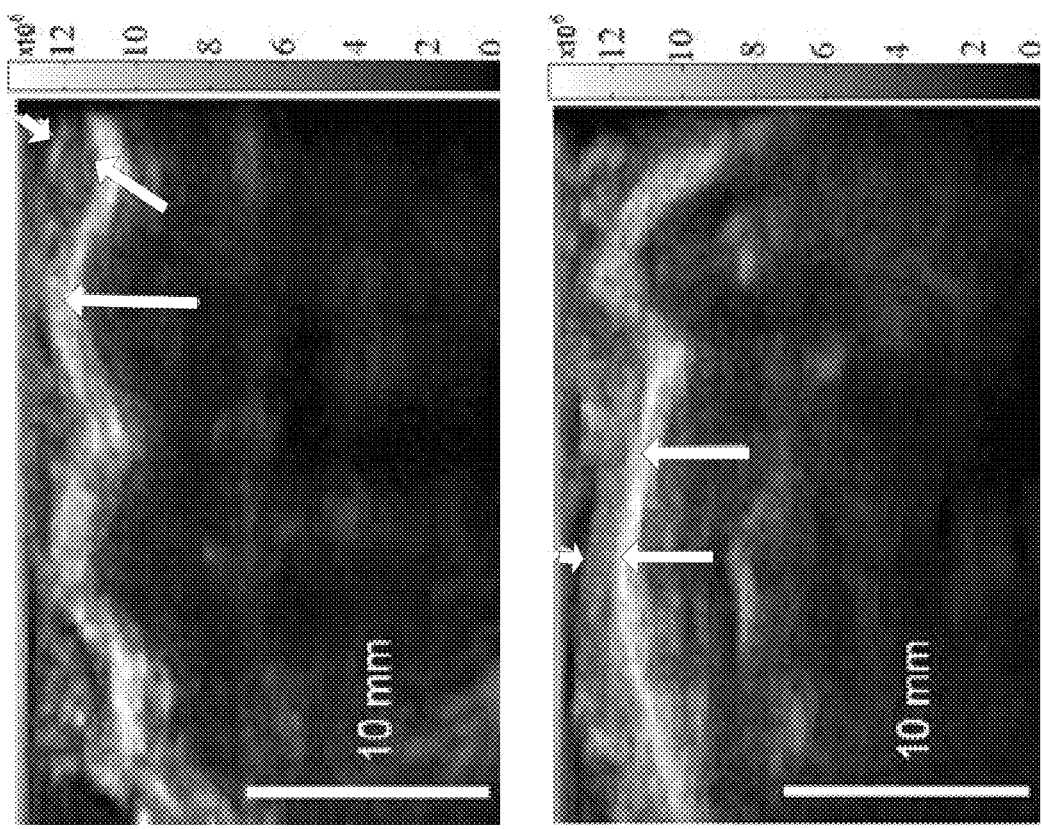
FIG. 10 is a collection of ultrasound images obtained using an intraoral probe during ultrasound scanning.

FIG. 10 is a collection of ultrasound images obtained using the intraoral probe during ultrasound scanning. The images show a cross sectional view of the lower jaw (top image in FIG. 10) and upper jaw (bottom image in FIG. 10), specifically the gingival tissue and bone boundaries. An operating frequency of 10 MHz is used to obtain high resolution images. The gingival tissue is marked by the two opposing arrows, and it is apparent that the tissue is intact and no detachments appear, which suggests a healthy gingiva. Also in the figure, the bone boundary is marked by the single arrow. Once more, the bone boundary appears as a very bright contour (in the original image), because of the high acoustic reflectivity exhibited by the bone.

In addition, the gingival tissue is observed to be clearer in this case than the extraoral imaging. The fact that the probe is nearly touching the gingiva made this imaging technique give more emphasis on the soft tissue, and it appears very clear compared to the extraoral images. Furthermore, thickness measurements are reported to be easier to obtain, as the measurement starts directly from the top of the images. In this example, the whole imaging procedure took 5-10 minutes for each region of interest. It is also noted that the intraoral probe is easier to maneuver around the imaging region of interest. Also, some embodiments of the intraoral probe feature an ergonomic handle to provide better control and stability for the operator.

Due to the easy maneuverability of the intraoral probe, 3D imaging of the gingiva can be constructed by embodiments of the imaging system 100. By carefully rotating the linear probe around its central axis in the elevational direction in front of the gingival tissue, to simulate a rocking motion in a manual manner, 3D volumes of the soft tissue can be constructed. In one embodiment, a motor driven rocking linear array intraoral probe is featured to provide improved measurements and assessments.

During testing, this rocking technique was applied on the lower jaw of a human subject. The produced frames were stored as a three dimensional array in the memory of the imaging system 100. The array was then post processed, scan converged in the elevational direction, and image slices were co-registered together to produce an approximate volume of the soft tissue.

In one implementation, a resultant volume rendering shows the high peaks associated with the soft tissue and bone boundary. This imaging feature has the advantage of better visualizing the soft tissue and giving more information about the health of the gum. The use of 3D imaging helps more accurate thickness measurements, by making markers that ensure same location of measurement each time. Also the markers help to localize the same point of tissue in the following up process of the gingival tissue health and its attachment status to the bone.

In assessing the extraoral and intraoral imaging techniques, both extraoral and intraoral imaging exemplary processes were performed at relatively shallow depths, 2.5 and 2 centimeters respectively. As a result, attenuation effects were minimal and that eliminates the need for any additional image post processing steps such as adaptive gain compensations. The fact that intraoral imaging was performed at a shallower depth provided higher intensity ultrasound echoes with less attenuation effects. No shadowing effects appeared in the regions of interest as shown in the presented images. Therefore, with the proper use of adequate amounts of coupling materials, shadowing effect may be eliminated. In addition, shadowing occurs generally only below the tooth boundary in the in vivo images, where there are no useful visible features in the images, as soft tissues were not present.

Figure 11:
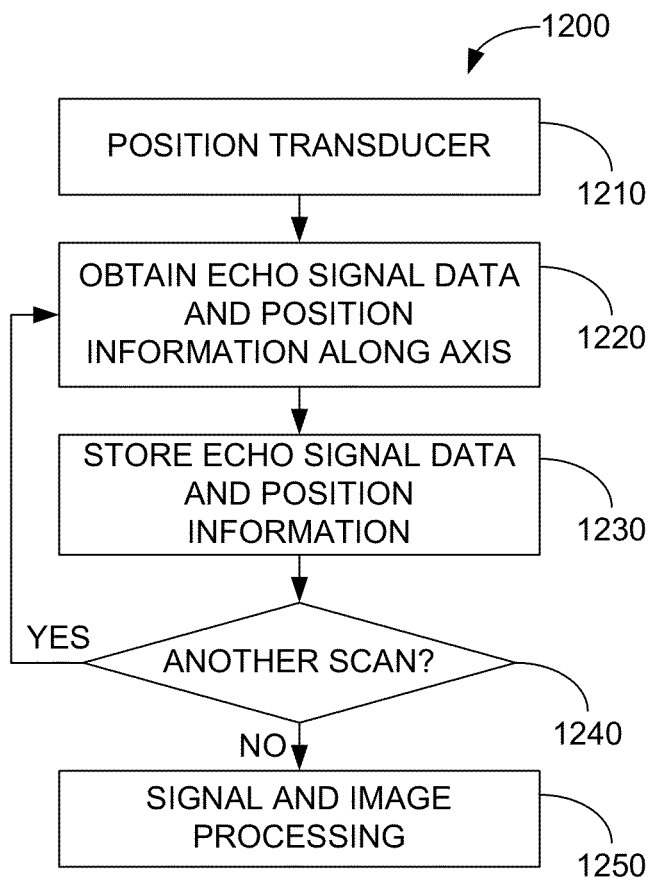

With reference to FIG. 11, shown is a flow chart 1200 illustrating the acquisition of echo signal data using an echoperiodontal imaging system 100 in accordance with various embodiments of the disclosure. The transducer 110 (or transducer array 210) is initially positioned in block 1210 with respect to the jaw. In some embodiments, the transducer 110 is positioned at a corner of the FOV where the scan begins. In other embodiments, the transducer 110 is positioned at an initial alignment position (e.g., the center of the FOV) and the transducer 110 is relocated to the corner of the FOV.

Echo signal data and the corresponding position information are obtained along an axis in block 1220. The axis may be in the lateral or elevation direction. The echo signals may be processed (e.g., filtering, amplification, compression, and/or analog beamforming for arrays) before digitizing the signals. After the information is obtained along the axis, the digitized data is stored in memory or on a computer-readable storage medium in block 1230. While the exemplary flow chart 1200 of FIG. 11 indicates storing the echo signal data and corresponding position information after scanning is complete, in some embodiments echo signal data is stored as it is obtained.

It is then determined in block 1240 whether another scan along the axis is to be performed. In the case of a two-dimensional scan with a single transducer 110 or a one-dimensional transducer array 210, the positioning system 160 relocates the transducer 110 (or 210) and returns to block 1220 to obtain the echo signal data and the corresponding position information along the newly offset axis (next row or column) within the FOV. If a two-dimensional transducer array 210 is used, the next set of information along the axis may be obtained without relocation of the transducer array.

When the ultrasonic scan has been completed for the FOV or if only a one-dimensional scan is to be performed, the stored echo signal data and corresponding position information may then be processed and used for image processing in block 1250. To this end, the imaging system controller 150 of the imaging system 100 of FIG. 1 may provide signal processing of the acquired echo signal data. Alternatively, a separate computer may provide the signal processing.

Figure 12:
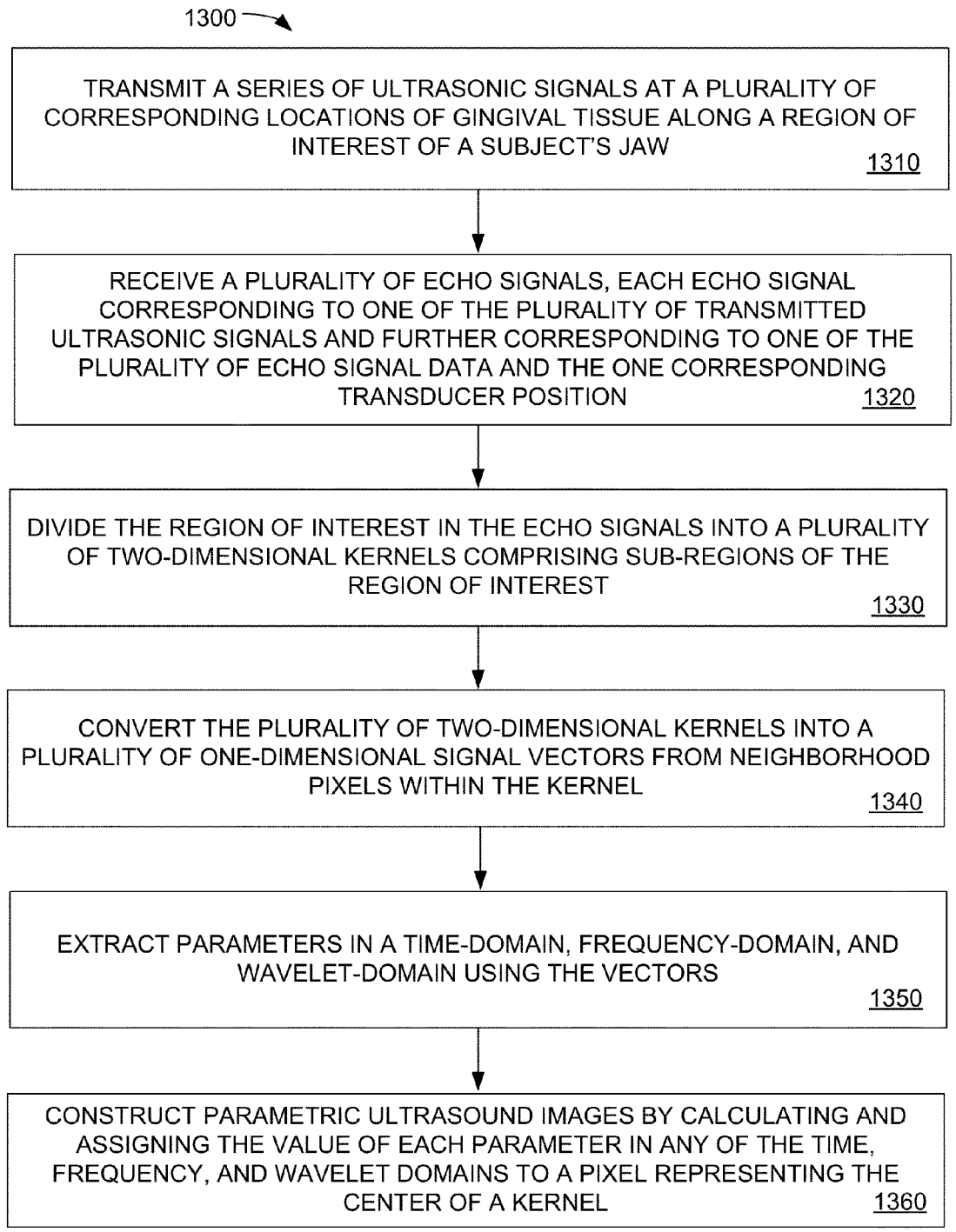

Referring now to FIG. 12, shown is a flow chart 1300 illustrating the processing of ultrasound images using an echoperiodontal imaging system 100 in accordance with various embodiments of the disclosure. In block 1310, a series of ultrasonic signals are transmitted by the transducer 110 (or 210) at a plurality of corresponding locations of gingival tissue along a region of interest of a subject's jaw. Next, the transducer 110 (or 210) receives a plurality of echo signals, where each echo signal corresponds to one of the plurality of transmitted ultrasonic signals and further corresponds to one of the plurality of echo signal data and the one corresponding transducer position, in block 1320. During image processing, the imaging system 100 divides the region of interest in the echo signals into a plurality of two-dimensional kernels comprising sub-regions of the region of interest, in block 1330. Next, in block 1340, the imaging system 100 converts the plurality of two-dimensional kernels into a plurality of one-dimensional signal vectors from neighborhood pixels within the kernel and extracts parameters in a time-domain, frequency-domain, and wavelet-domain using the vectors, in block 1350. Then, in block 1360, parametric ultrasound images are constructed by calculating and assigning the value of each parameter in any of the time, frequency, and wavelet domains to a pixel representing the center of a kernel.

Next in FIG. 13, a diagram of a flow chart illustrating an embodiment of a method for in vitro acquisition of ultrasound images using an echoperiodontal imaging system 100 is presented. First, in block 1410, a sample is positioned in degassed water near the ultrasound transducer focus for scanning with the free gingival surface of the sample facing the ultrasound transducer 110 (or 210). Sequential ultrasound scans are performed parallel to the base of the sample to render cross-sectional ultrasound images in the occlusal plane, in block 1420. Then, in block 1430, hyper-echoic and hypo-echoic regions in the ultrasound images are detected to identify periodontal defects in the gingival tissue.

Figure 14:
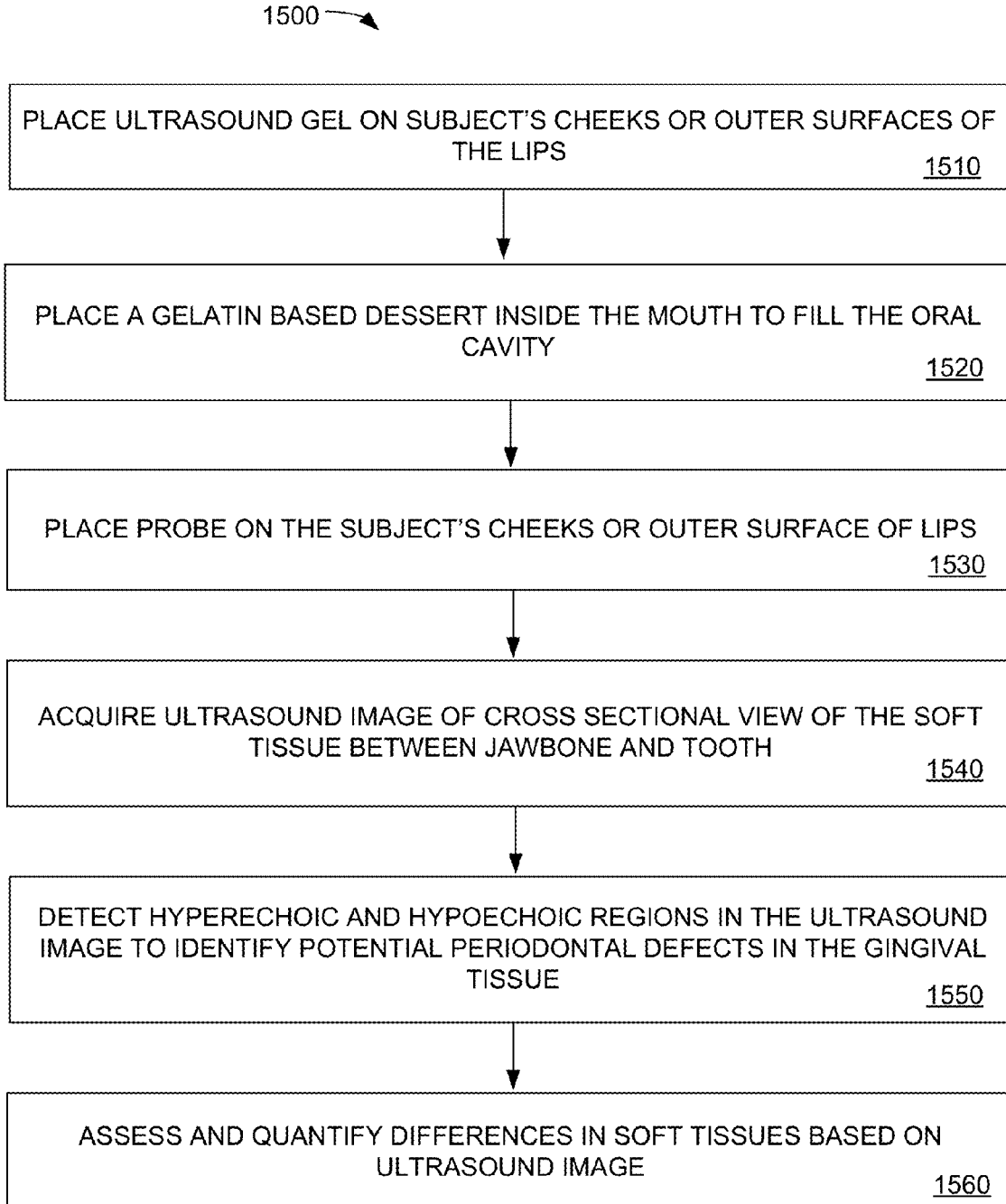

Referring now to FIG. 14, a diagram of a flow chart illustrating an embodiment of a method for in vivo acquisition of ultrasound images using an echoperiodontal imaging system 100 with an extraoral probe is depicted. For an exemplary case of extraoral imaging testing, 9.5 MHz linear array probe with a 4 cm footprint size is used, but not limited to being used, in imaging, in one embodiment, where the probe is an end fire type probe. In other embodiments, a linear array 5-14 MHz ultrasound transducer, phased, and curvilinear arrays can also be used as extraoral probes.

In block 1510 of FIG. 14, ultrasound gel is placed on a subject's cheeks or outer surfaces of the lips. Further, in block 1520, a gelatin based dessert is placed inside the mouth to fill the oral cavity, and the extraoral probe is placed on the subject's cheek or outer surface of the lips, in block 1530. The gelatin is used to obtain an acoustic impedance match between the probe and the inner soft tissue, and also to eliminate air bubbles. An ultrasound image of a cross sectional view of the soft tissue between the subject's jawbone and adjacent tooth is then acquired by the imaging system 100, in block 1540. In one embodiment, to acquire the ultrasound image, the probe's operating frequency is set to 10 MHz to obtain high resolution images. From the acquired image, hyper-echoic and hypo-echoic regions in the ultrasound image are detected to identify periodontal defects in the gingival tissue, in block 1550.

Figure 15:
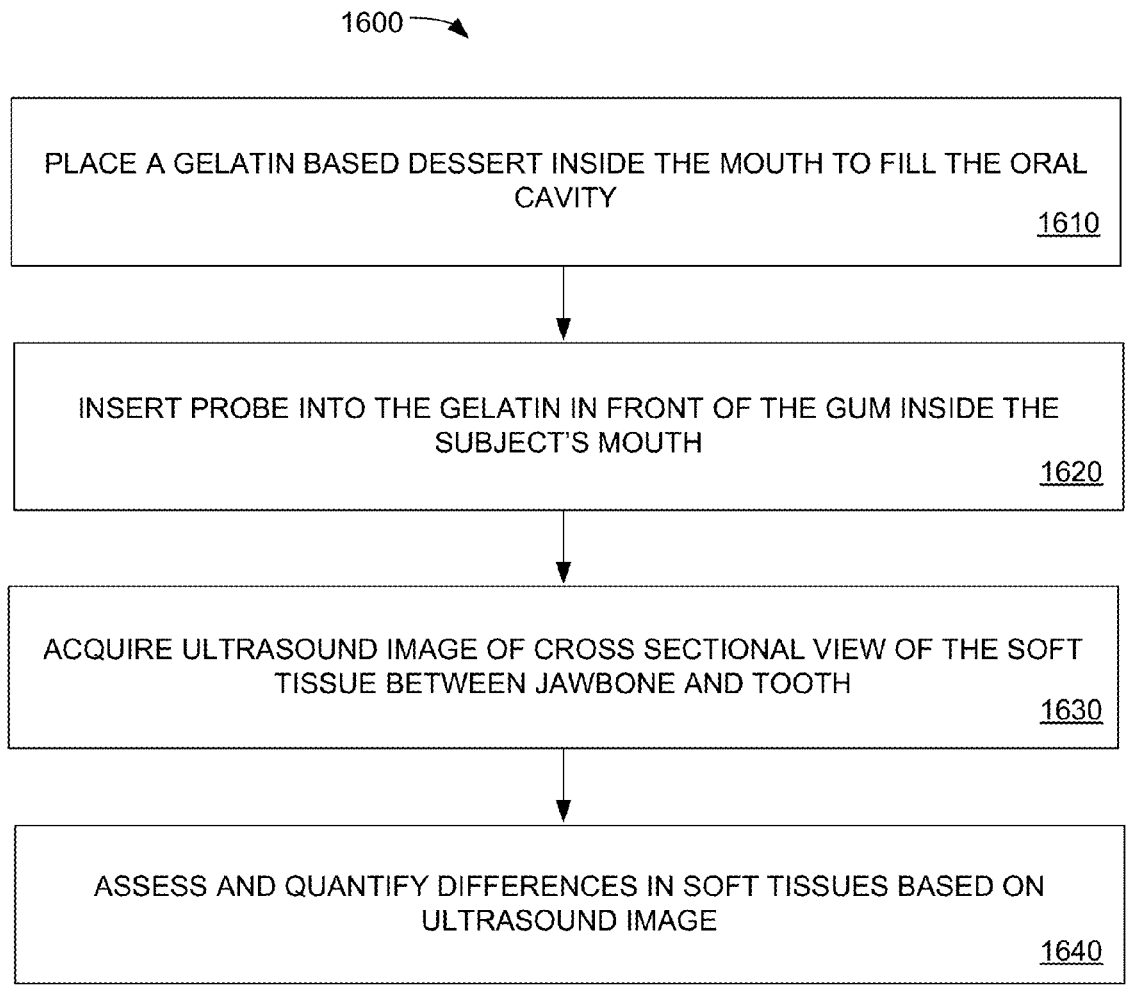

Referring now to FIG. 15, a diagram of a flow chart illustrating an embodiment of a method for in vivo acquisition of ultrasound images using an echoperiodontal imaging system 100 with an intraoral probe is depicted. In block 1610, a gelatin based dessert is placed inside the mouth of a subject to fill the oral cavity, and the intraoral probe is inserted into the gelatin in front of the gum inside the subject's mouth, in block 1620. An ultrasound image of a cross sectional view of the soft tissue between the subject's jawbone and adjacent tooth is then acquired by the imaging system 100, in block 1630. From the acquired image, differences in soft tissues based on ultrasound image are assessed and/or quantified, in block 1640.

Figure 16:
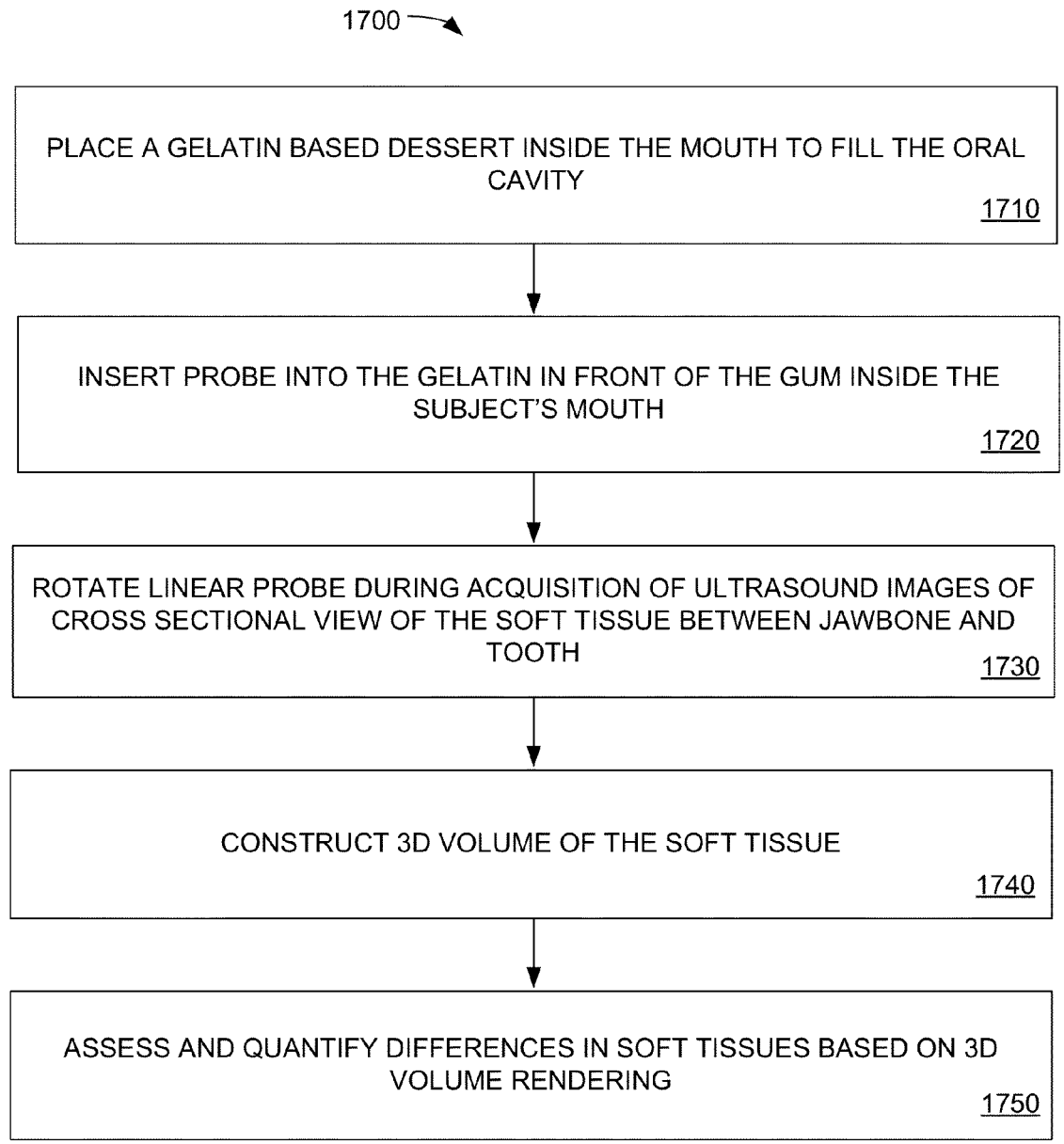

In FIG. 16, a diagram of a flow chart illustrating an embodiment of a method for in vivo acquisition of 3D ultrasound images using an echoperiodontal imaging system 100 with an intraoral linear probe is depicted. In block 1710, a gelatin based dessert is placed inside the mouth of a subject to fill the oral cavity, and the intraoral linear probe is inserted into the gelatin in front of the gum inside the subject's mouth, in block 1720. During ultrasonic scanning by the imaging system 100, the intraoral linear probe is rotated, in block 1730. Ultrasound images of a cross sectional view of the soft tissue between the subject's jawbone and adjacent tooth is acquired by the imaging system 100 and used to construct a 3D volume rendering of the soft tissue, in block 1740. Differences in soft tissues are assessed and/or quantified based on the 3D volume rendering, in block 1750.

Embodiments of the imaging system 100 or portions of the imaging system 100 can be implemented in software (e.g., firmware), hardware, or a combination thereof. Generally, in terms of hardware architecture, the imaging system 100 includes a processor, memory, and one or more input and/or output (I/O) devices (or peripherals) that are communicatively coupled via a local interface. The processor is a hardware device for executing software, particularly that stored in memory. The processor can be any custom made or commercially available processor, a central processing unit (CPU), an auxiliary processor among several processors associated with the imaging system controller 150, a semiconductor based microprocessor (in the form of a microchip or chip set), a macroprocessor, or generally any device for executing software instructions. The memory can include any one or combination of volatile memory elements (e.g., random access memory (RAM, such as DRAM, SRAM, SDRAM, etc.)) and nonvolatile memory elements (e.g., ROM, hard drive, tape, CDROM, etc.). Moreover, the memory may incorporate electronic, magnetic, optical, and/or other types of storage media. Note, that the memory can have a distributed architecture, where various components are situated remote from one another, but can be accessed by the processor. The software in memory may include one or more separate programs, each of which comprises an ordered listing of executable instructions for implementing logical functions. In one embodiment, the software in the memory includes logical functions representative of block(s) shown in the flow chart(s) described above and a suitable operating system (O/S). It should be noted that logical functions representative of block(s) shown in the flow chart(s) can be stored on any computer readable medium for use by or in connection with any computer related system or method.

In the context of this document, a computer readable medium is an electronic, magnetic, optical, or other physical device or means that can contain or store a computer program for use by or in connection with a computer related system or method. In the context of this document, a "computer-readable medium" can be any means that can store, communicate, or transport the program for use by or in connection with the instruction execution system, apparatus, or device. The computer readable medium can be, for example but not limited to, an electronic, magnetic, optical, electromagnetic, infrared, or semiconductor system, apparatus, or device medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical).

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, at least the following is claimed:

1. A system for echoperiodontal imaging of gingival tissue, comprising:
    a transducer adapted to:
        be positioned along a plurality of locations of gingival tissue for a region of interest of a jaw;
        transmit a series of ultrasonic signals at the plurality of locations of the gingival tissue for the region of interest of the jaw, and
        receive a plurality of echo signals, each echo signal corresponding to one of the transmitted ultrasonic signals at one of the plurality of locations of the gingival tissue; and
    imaging system computer hardware configured to:
        coordinate transmission of the series of ultrasonic signals and reception of the corresponding echo signals,
        obtain a plurality of echo signal data of the gingival tissue and a plurality of transducer positions, where each echo signal data corresponds to one of the plurality of transducer positions and is derived from the received plurality of echo signals;
        dividing a region of interest in the echo signals of the plurality of corresponding locations into a plurality of two-dimensional kernels comprising sub-regions of the region of interest;
        convert each of the plurality of two-dimensional kernels into a plurality of one-dimensional signal vectors from neighborhood pixels within a two-dimensional kernel and the one-dimensional signal vectors are used to extract parametric values in a time-domain, a frequency-domain, and a wavelet-domain; and
        reconstruct at least a two-dimensional image of a portion of the gingival tissue of the jaw based upon the obtained echo signal data, the plurality of transducer positions, and the parametric values from at least the time-domain, the frequency-domain, and the wavelet-domain, wherein the at least a two-dimensional image comprises a parametric ultrasound image with pixel values represented using the parametric values from the time-domain, the frequency-domain, and the wavelet-domain.

2. The system of claim 1, wherein the imaging system computer hardware provides access to B-mode images.

3. The system of claim 1, wherein the kernels overlap in space by approximately 90%.

4. The system of claim 1, wherein the imaging system computer hardware is further configured to construct parametric ultrasound images by calculating and assigning a value of each parameter in any of the time, frequency, and wavelet domains to a pixel representing a center of the two-dimensional kernel.

5. The system of claim 1, wherein the transducer comprises an extraoral probe that is positioned outside a mouth of a human subject.

6. The system of claim 1, wherein the transducer comprises a linear array side intraoral probe that is positioned inside a mouth of a human subject.

7. The system of claim 1, wherein the transducer is a transducer array.

8. The system of claim 1, wherein the image is a three-dimensional volume rendering of the gingival tissue of the jaw.

9. A method for echoperiodontal imaging, comprising:
positioning a transducer adjacent to a jaw of a subject;
transmitting a series of ultrasonic signals at a plurality of corresponding locations along the jaw of the subject;
receiving a plurality of echo signals, each echo signal corresponding to one of the transmitted ultrasonic signals;
obtaining a plurality of echo signal data and a plurality of corresponding transducer positions, where each echo signal data corresponds to one of the plurality of transducer positions and is derived from the received plurality of echo signals;
dividing a region of interest in the echo signals of the plurality of corresponding locations into a plurality of two-dimensional kernels comprising sub-regions of the region of interest;
for each one of the plurality of two-dimensional kernels, converting a two-dimensional kernel into a plurality of one-dimensional signal vectors from neighborhood pixels within the two-dimensional kernel;
extracting parameters in a time-domain, a frequency-domain, and a wavelet-domain using the one-dimensional signal vectors; and
reconstructing at least two-dimensional image data of a portion of soft tissue adjacent to the jaw for display on a display device based upon the obtained plurality of echo signal data, the plurality of corresponding transducer positions, and parametric values from the time-domain, the frequency-domain, and the wavelet-domain, wherein the at least two-dimensional image data comprises a parametric ultrasound image with pixel values represented using the parametric values from the time-domain, the frequency-domain, and the wavelet-domain.

10. The method of claim 9, wherein the transducer is a one-dimensional transducer array.

11. The method of claim 9, wherein the transducer is a two-dimensional transducer array.

12. The method of claim 9, further comprising providing the image data for display of a three-dimensional volume rendering of the portion of the soft tissue of the jaw on the display device.

13. The method of claim 9, wherein the soft tissue comprises gingival tissue.

14. The method of claim 9, wherein the transducer is positioned external to a mouth of the subject.

15. The method of claim 9, wherein the transducer is positioned inside a mouth of the subject.

16. A method for echoperiodontal imaging, comprising:
transmitting a series of ultrasonic signals at a plurality of corresponding locations of gingival tissue along a region of interest of a jaw of a subject;
receiving a plurality of echo signals, each echo signal corresponding to one of the transmitted ultrasonic signals at one of the plurality of corresponding locations of gingival tissue;
dividing the region of interest in the echo signals into a plurality of two-dimensional kernels comprising sub-regions of the region of interest;
for each one of the plurality of two-dimensional kernels, converting a two-dimensional kernel into a plurality of one-dimensional signal vectors from neighborhood pixels within the two-dimensional kernel;
extracting parameters in a time-domain, frequency-domain, and wavelet-domain using the one-dimensional signal vectors; and
constructing parametric ultrasound images by calculating and assigning a value of each parameter in any of the time, frequency, and wavelet domains to a pixel representing a center of the two-dimensional kernel.

17. The method of claim 16, wherein the ultrasonic signals are transmitted by a transducer positioned outside a mouth of the subject.

18. The method of claim 16, wherein the ultrasonic signals are transmitted by a transducer positioned inside a mouth of the subject.

* * * * *